US007172868B2

(12) United States Patent
McCready et al.

(10) Patent No.: US 7,172,868 B2
(45) Date of Patent: Feb. 6, 2007

(54) **NUCLEOTIDE SEQUENCES SPECIFIC TO *FRANCISELLA TULARENSIS* AND METHODS FOR THE DETECTION OF *FRANCISELLA TULARENSIS***

(75) Inventors: Paula M. McCready, Tracy, CA (US); Lyndsay Radnedge, San Mateo, CA (US); Gary L. Andersen, Berkeley, CA (US); Linda L. Ott, Livermore, CA (US); Thomas R. Slezak, Livermore, CA (US); Thomas A. Kuczmarski, Livermore, CA (US); Elizabeth A Vitalis, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 362 days.

(21) Appl. No.: 10/630,154

(22) Filed: Jul. 29, 2003

(65) Prior Publication Data

US 2006/0040268 A1 Feb. 23, 2006

Related U.S. Application Data

(60) Provisional application No. 60/440,892, filed on Aug. 1, 2002.

(51) Int. Cl.
*C12Q 1/68* (2006.01)
*C12P 19/34* (2006.01)

(52) U.S. Cl. .......................................... 435/6; 435/91.2

(58) Field of Classification Search .................... 435/6, 435/91.2
See application file for complete search history.

(56) References Cited

FOREIGN PATENT DOCUMENTS

WO WO 97/11195 A1 3/1997

OTHER PUBLICATIONS

Prior R.G. et al: "Preliminary analysis and annotation of the partial genome sequence of *Francisella tularensis* strain Schu 4". Journal of Applied Microbiology, Oxford, vol. 91, No. 4, Oct. 2001, pp. 614-620.

Karlsson J. et al: "Sequencing of the *Francisella tularensis* Strain Schu 4 Genome Reveals The Shikimate and Purine Metabolic Pathways, Targets for the Construction of a Rationally Attenuated Auxotrophic Vaccine". Microbial and Comparative Genomics, Mary Ann Liebert, Larchmont, NY, US, vol. 5, No. 1, 2000, pp. 25-39.

Long G.W. et al: "Detection of *Francisella tularensis* in Blood by Polymerase Chain Reaction". Journal of Clinical Microbiology, Washington, DC, US, vol. 31, No. 1, 1993, pp. 152-154.

*Primary Examiner*—Mark Navarro
(74) *Attorney, Agent, or Firm*—John H. Lee

(57) ABSTRACT

Described herein is the identification of nucleotide sequences specific to *Francisella tularensis* that serves as a marker or signature for identification of this bacterium. In addition, forward and reverse primers and hybridization probes derived from these nucleotide sequences that are used in nucleotide detection methods to detect the presence of the bacterium are disclosed.

10 Claims, No Drawings

NUCLEOTIDE SEQUENCES SPECIFIC TO *FRANCISELLA TULARENSIS* AND METHODS FOR THE DETECTION OF *FRANCISELLA TULARENSIS*

RELATED APPLICATION

This application claims the benefit of U.S. Provisional Application No. 60/400,892, filed Aug. 1, 2002, and entitled, "DNA Diagnostics *Francisella Tularensis* Species," which is incorporated herein by this reference.

The United States Government has rights in this invention pursuant to Contract No. W-7405-ENG-48 between the United States Department of Energy and the University of California for the operation of Lawrence Livermore National Laboratory.

SEQUENCE LISTING IN COMPUTER READABLE FORM

The sequence listing information recorded in computer readable form is identical to the written on paper sequence listing.

BACKGROUND

*Francisella tularensis* is the species of bacteria known to cause what is commonly known as Tuleremia, a serious and sometimes fatal disease. Since the attack on the World Trade Center in New York of Sep. 11, 2001, there has been a growing concern that terrorists or rogue governments will use the *Francisella tularensis* bacterium as a weapon of mass destruction and instrument of terror. Since the events of Sep. 11, 2001, the United States Government has been developing reliable methods and systems to detect the *Francisella tularensis* bacterium so that immediate and effective counter measures can be undertaken. The existing methods for detecting the *Francisella tularensis* bacterium are considered inadequate because of the higher than acceptable rate of false positive and false negative results. False positive results lead to confusion regarding whether the *Francisella tularensis* bacterium is actually present and whether protective measures should immediately be implemented. Conversely, false negative results would allow the *Francisella tularensis* bacterium to remain undetected with consequent adverse impacts. A more reliable method of detecting the *Francisella tularensis* bacterium would reduce the occurrence of false positive and false negative results and provide decision makers with greater confidence in implementing appropriate counter measures.

SUMMARY OF THE INVENTION

An aspect of the invention includes the nucleotide sequences that are identified in SEQ ID NOs:4, 8, 12, 16, 20, 24, 28 and 32 that are specific to *Francisella tularensis*.

Another aspect of the invention includes a Forward Primer, the nucleotide sequences that are identified in SEQ ID NOs:1, 5, 9, 13, 17, 21, 25, and 29 and any primers that are derived from these nucleotide sequences.

A further aspect of the invention is a Reverse Primer, the nucleotide sequences that are identified in SEQ ID NOs:2, 6, 10, 14, 18, 22, 26 and 30 and any primers that are derived from these nucleotide sequences.

A further aspect of the invention is includes a Hybridization Probe, the nucleotide sequences that are identified in SEQ ID NOs:3, 7, 11, 15, 19, 23, 27 and 31 and any probes that are derived from these nucleotide sequences.

This invention also includes a method for the detection of *Francisella tularensis* using the bacterium specific nucleotide sequence comprising: providing a sample in an environment that is suitable for isolating genomic DNA for amplification using PCR and under conditions suitable for hybridization with a least one group of nucleotides consisting or forward primer, a reverse primer and a hybridization probe and detecting the existence of *Fracisella Tularensis* specific nucleotide sequences by a nucleotide detection method, such as PCR and flurogenic 5' nuclease PCR assay, wherein the existence of the nucleotide sequence indicates the presence of *Francisella tularensis* in the sample.

| BRIEF DESCRIPTION OF THE SEQUENCES | |
|---|---|
| SEQ ID NO: 1 | Primer |
| SEQ ID NO: 2 | Primer |
| SEQ ID NO: 3 | Probe |
| SEQ ID NO: 4 | Amplicon |
| SEQ ID NO: 5 | Primer |
| SEQ ID NO: 6 | Primer |
| SEQ ID NO: 7 | Probe |
| SEQ ID NO: 8 | Amplicon |
| SEQ ID NO: 9 | Primer |
| SEQ ID NO: 10 | Primer |
| SEQ ID NO: 11 | Probe |
| SEQ ID NO: 12 | Amplicon |
| SEQ ID NO: 13 | Primer |
| SEQ ID NO: 14 | Primer |
| SEQ ID NO: 15 | Probe |
| SEQ ID NO: 16 | Amplicon |
| SEQ ID NO: 17 | Primer |
| SEQ ID NO: 18 | Primer |
| SEQ ID NO: 19 | Probe |
| SEQ ID NO: 20 | Amplicon |
| SEQ ID NO: 21 | Primer |
| SEQ ID NO: 22 | Primer |
| SEQ ID NO: 23 | Probe |
| SEQ ID NO: 24 | Amplicon |
| SEQ ID NO: 25 | Primer |
| SEQ ID NO: 26 | Primer |
| SEQ ID NO: 27 | Probe |
| SEQ ID NO: 28 | Amplicon |
| SEQ ID NO: 29 | Primer |
| SEQ ID NO: 30 | Primer |
| SEQ ID NO: 31 | Probe |
| SEQ ID NO: 32 | Amplicon |

DETAILED DESCRIPTION

Disclosed herein are nucleotide sequences located on different loci of the *Francisella tularensis* bacterium genome, and primers and the hybridization probes used in detecting the specific nucleotide sequences. Also disclosed is a method for identifying *Francisella tularensis* by analyzing samples taken from monitoring devices, such as air monitors, for the nucleotide sequences that are specific to *Francisella tularensis*. As the nucleotide sequences that have been identified are unique to the *Francisella tularensis* bacterium, using the primers and hybridization probes to detect the presence of the *Francisella tularensis* bacterium is far more reliable than existing methods and partly reduces the occurrence of false positive and false negative results.

*Francisella tularensis* is the bacterium that causes Tularemia, a disease that can be fatal if not detected and treated with appropriate antibiotics. The symptoms of Tularemia "could include sudden fever, chills, headaches, muscle aches, joint pain, dry cough, progressive weakness, and pneumonia", this information can be found at the CDC website. It is on the Center for Disease Control and Prevention (CDC) list of possible bacteria that has potential as a biological warfare weapon. The CDC has developed a list of possible pathogens that may be used as weapons of mass destruction. *Francisella tularensis* has been listed in Category A of possible diseases and agents. Those diseases and agents in Category A are considered a high risk to national security because they "can be easily disseminated or transmitted from person to person; result in high mortality rates and have the potential for major public health impact; might cause public panic and social disruption; and require special action for public health preparedness ". as Quoted at the CDC website.

A key element in developing defenses against the use of *Francisella tularensis* is the ability to quickly and accurately detect the presence of the bacterium. Early detection will allow for the implementation of effective counter measures. Additionally, early detection will allow for the identification and treatment of those that may have been exposed to the bacterium. Early detection and treatment is essential for the treatment of Tularemia because although the disease may be fatal, it is usually treatable with antibiotics upon early detection.

Existing detection methods have resulted in a higher than acceptable rate of false positive and false negative results. Such results are inadequate and can create confusion regarding the appropriate countermeasures, if any, that should be undertaken because it is unclear whether the bacterium is present or not. If the bacterium is not present, undertaking counter measures may cause undue expense and create unwarranted concern among those that may incorrectly believe they have been exposed.

Although the genome for *Francisella tularensis* has already been mapped, this alone is not sufficient to develop a reliable and accurate detection mechanism because the current methods use nucleotide sequences that may be common to many different bacteria. Thus, existing detection methods could not distinguish between various bacteria, which results in higher than acceptable false positive detection rates. Similarly, some existing detection methods result in false negative results because they are not sensitive enough to detect the bacterium.

Using a nucleotide sequence that is specific to results in a more reliable detection method.

In order to detect any of the eight amplicons specific to *Francisella tularensis*, a series of forward and reverse primers and hybridization probes were developed for each of the eight amplicons.

A typical assay can determine the presence of SEQ ID Nos 4 and 8 using the sequence specific primers and the hybridization probes. If there is a positive result for the presence of *Francisella tularensis* then an assay is run to determine the presence of additional amplicon sequences, as a means to double check for the presence of *Francisella tularensis*.

Identifications of the *Francisella tularensis* specific nucleotide sequences allows the presence of the bacteria to be detected from environmental samples using PCR assay analysis and detection. PCR is a technique utilized to amplify genomic DNA. Typical PCR reactions include appropriate PCR buffers, nuclease polymerase and one or more oligonucleotide primers and hybridization probes. Various modifications of PCR techniques are possible as detailed in *Current Protocols in Molecular Biology* ed. F. M. Ausubel, R. Brent, D. D. Moore, K. Struhle, Massachusetts General Hospital and Harvard Medical School (1987) which is hereby incorporated by reference. The following US patents describe PCR and are incorporated herein by reference: U.S. Pat. No. 4,683,195; U.S. Pat. No. 4,683,202; U.S. Pat. No. 4,800,159.

One method that may be used for real-time PCR amplification and detection is TaqMan®. The principles involved in the conventional Taqman® 5' exonuclease assay are described in detail by Holland et al in, *Detection of specific polymerase chain reaction product by utilizing the 5'—3' exonuclease activity of Thermus aquaticus polynucleotide polymerase*, Proc Natl Acad Sci USA 88 (16):7276–80, 1991, which is herein incorporated by reference. TaqMan® real time detection can also be used to simultaneously detect a plurality of nucleic acid targets when it is used with multiplex PCR, which enables simultaneous detection of more than one target sequence, thus enhancing detection accuracy. A few examples of typical PCR instruments include the ABI prism 7700, the Cepheid Smart Cycler, and the Bio-Rad iCycler. In order to use a PCR assay method for detection of the *Francisella tularensis* bacterium, the sample must be prepared to extract all DNA that may be present. The following is a protocol for the preparation of samples taken from ambient air monitoring devices for nucleotide detection using fluorogenic 5' nuclease PCR assay.

Assay Protocol

Definitions:

DNA—deoxyribonucleic acid

EDTA—ethylenediaminetetraacetic acid

PCR—polymerase chain reaction

PCR water—autoclaved water, then filtered

CT—cycle threshold—the cycle in which the fluorescence signal crosses a user defined threshold FAM—reporter dye TAMRA—quencher dye Sample Preparation:

Exposed environmental filters are suspended in Sodium phosphate/EDTA, Tween buffer and bead beaten. The supernatant is filtered and washed to yield the genomic DNA extract. The extract is then subjected to real-time polymerase chain reaction (PCR) assay using a fluorescent-labeled probe. This process monitors a PCR reaction and the quantity of double-stranded product that is produced Materials Needed:

A series of forward and reverse primers, a hybridization probe and polymerase reagents specific to the first amplicon to be detected. A series of forward and reverse primers, a hybridization probe and polymerase reagents specific to the second amplicon to be detected.

Bead beater Kit with the following labeled components:

a. 3 capped tubes containing a filter and beads
b. 3 yellow ultra free MC Centrifugal Filter Units
c. 6 blue microcon YM-100 filter units
d. 12 collection tubes
e. 7 PCR reaction mix-includes primer/probe and Taq-labeled A,B,C,D,E,F,G
f. 48–25 μl Smart Cycle reaction tubes
g. Sodium phosphate buffer/EDTA Teen buffer
h. PCR water
i. Inhibitory control DNA
j. Extra unlabeled tubes Materials not provided in the bead beater kit:

a. Cepheid Smart Cycle
b. Microcentrifuge
c. Microfuge for Cepheid tubes

Preparation of DNA Extract:

This part of the assay protocol is performed in segregated work areas and in a biosafety cabinet using BSL 2 practices.

1. Add 400 μl of Sodium phosphate/ED TA Teen buffer to each of the capped tubes containing a filter and beads. Screw cap tightly.
2. Insert tubes one at a time into the bead beater.
3. Bead beat the capped tube for 3 minutes and a speed of 5000 rpm.
4. Remove capped tube from bead beater and place the tube on ice for a minimum of 2 minutes to cool.
5. Wash Steps.

Spin capped filter tubes for 10 seconds (pulse spin) in microcentrifuge.

Transfer approximately 400 μl of the supernatant to the yellow top filter collection tube.

Spin the yellow top filter tube with the supernatant @ 7000 rpm for 3 minutes.

Transfer the filtered liquid to a blue microcon filter on collection tube #1.

Spin @ 7000 rpm for 1 minute. Check fluid level in the blue microcon filter. If it is above the white base, pulse spin for about 10 seconds to bring the level at or a little below the white area. It could take more than one pulse spin to bring the level down. This is approximately 100–200 μl of liquid.

Transfer this liquid on the top of the filter to a second blue microcon filter on a clean collection tube #2. Tilt the tube at a 45° angle and take off the liquid-do NOT vacuum the filter.

Add 400 μl of PCR water to the second blue microcon filter with the added liquid.

Spin @ 7000 rpm for 2 minutes. Do not be spin dry; there should be about 50–100 μl of liquid on top of the filter. Pulse spin if the level is too high Using clean, metal forceps remove the blue microcon filter from the collection tube #2 and place the blue microcon filter on a clean collection tube #3. Discard collection tube #2.

Add 400 μl PCR water to the blue microcon filter on collection tube #3.

Spin @ 7000 rpm for 2 minutes. Do not be spin dry; there should be about 50–100 μl of liquid on top of the filter. Pulse spin if the level is too high.

Remove the blue microcon filter. Place the blue microcon filter on collection tube #4. Discard collection tube #3

Add 400 μl PCR water to the blue microcon filter on collection tube #4.

Spin for 1 minute @ 7000 rpm. Check fluid level in the blue microcon filter. If it is above the white base, pulse spin for about 10 seconds to bring the level at or a little below the white area. This could take more than one pulse spin. If the level of liquid is at or a little below the white base, this is approximately 100–200 μl of DNA extract. If for some reason the pulse spin has brought the level of DNA extract down too low add 200 μl PCR water and bring the level carefully to the white base level by pulse spinning for less time).

Transfer the liquid on the top of the blue microcon filter (your DNA extract) to the eppendorf tube.

If you cannot perform the PCR assay immediately, keep extract refrigerated.

PCR Assay:

1. Thaw on ice each set of primer/probe/Taq polymerase sets. Once thawed PCR assay must begin. Do NOT refreeze. Keep on ice while testing.
2. Add 20 μl of each of the PCR reaction mixes for each amplicon and one inhibitory control to the appropriately labeled Cepheid reaction tubes; e.g. 1–1A is for amplicon 1, filter 1, a set of primers, probe, Taq polymerase.
   a. Add 5 μl of DNA extract to each of the tubes-rinse tip1–2 times in the mix and discard the tip.
   b. Use a clean tip for each reaction tube.
   c. Each tube should have a total of 25 μl .
3. Add 15 μl of PCR reaction inhibitory mix to appropriately labeled Cepheid tubes; e.g INHIB.
   a. Add 5 μl DNA extract to each tube-rinse tip 1–2 times in the mix and discard tip.
   b. Add 5 μl of DNA inhibitory control to each tube-rinse tip 1–2 times in the mix nd discard the tip.
   a. Use a clean tip for each reaction tube.
   b. Each tube should have a total of 25 μl .
4. Include as controls:

NTC (no template control) for each set of primers/probe, Taq.
5. Spin Cepheid tubes in Cepheid microfuge for about 4 seconds. This mixes the PCR reaction mix and DNA into the optic diamond area. Check to see that the optic area is filled.

Run Cepheid Smart Cycler

Record all CT values (including 0) on the result sheet for the appropriate organism and filter.

6. CT values from 34 to 35 indicate negative readings—no *Francisella* DNA detected. CT values below 34 indicate positive readings—*Francisella* DNA detected.

Table 1 shows the results of assay runs that were performed using the above described protocol. An assay set containing the primers and probe for each amplicon sequence was added to a sample containing either the *Francisella tularensis* bacteria or *Francisella philomiragia*. The *Francisella philomiragia* bacteria is similar in genetic composition to its cousin *Francisella tularensis*. *Francisella philomiragia* was, therefore, used as a control to demonstrate that the primers and probe derived from the *Francisella tularensis* specific amplicon could distinguish between genetic near neighbors, thereby demonstrating the specificity of the amplicon sequence. Three different strains of the *philomiragia* bacteria were used, 25016, 25017 and 25018. The *Francisella tularensis* and the *Francisella philomiragia* DNA was obtained form American Type Culture Collection. The assay sets containing the probes and primers were obtained from various vendors such as ABI and Biosearch.

All assays were run three times with the exception of *Francisella philomiragia* #25018 which was run twice. The results show that the assay runs having the *Francisella tularensis* DNA in the sample had positive results, CT values of less than 34. Those assay runs having *Francisella philomiragia* in the sample had negative results, CT values of 34 to 35. These results show that the primers and probe derived from the *Francisella tularensis* specific amplicon can distinguish between near genetic neighbors of the *Francisella* bacteria, thus demonstrating that the nucleotide sequences in the amplicons are specific to *Francisella tularensis*.

| ft5698r2C106.tF: Seq. ID No. 21, 22, 23 | 35 | 35 | 35 | 35 | 35 | 35 | 35 | 35 |
|---|---|---|---|---|---|---|---|---|
| ft5698r2C127.tF: Seq. ID No. 25, 26, 27 | 35 | 35 | 35 | 35 | 35 | 35 | 35 | 35 |
| ft5698r2C86.tF: Seq. ID No. 29, 30, 31 | 35 | 35 | 35 | 35 | 35 | 35 | 35 | 35 |

The nucleotide sequences disclosed herein are specific to *Francisella tularensis*. Accordingly, although air monitors are an effective method of obtaining samples for analyses, a wide variety of other media and methods may be used to provide the samples for analysis for the *Francisella tularensis* bacterium.

All numbers expressing quantities of ingredients, constituents, reaction conditions, and so forth used in the specification and claims are to be understood as being modified in all instances by the term "about". Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for detection of *Francisella tularensis* in a sample comprising using a PCR assay to detect a first Amplicon consisting of SEQ ID NO:4 and a second Amplicon consisting of SEQ ID NO:8 in the sample, wherein detection of the first and second Amplicons in the sample indicates the presence of *Francisella tularensis* in the sample.

2. The method of claim 1, wherein said assay is a fluorogenic 5' nuclease PCR assay.

3. The method of claim 2, wherein said assay is performed using a first forward primer consisting of SEQ ID NO: 1, a first reverse primer consisting of SEQ ID NO:2, and a first hybridization probe consisting of SEQ ID NO:3 for detection of the first Amplicon and using a second forward primer consisting of SEQ ID NO:5, a second reverse primer consisting of SEQ ID NO:6, and a second hybridization probe consisting of SEQ ID NO:7 for detection of the second Amplicon.

4. The method of claim 1, comprising using the assay to detect a third Amplicon consisting of SEQ ID NO:12 and a fourth Amplicon consisting of SEQ ID NO:16 and a fifth Amplicon consisting of SEQ ID NO:20 and a sixth Amplicon consisting of SEQ ID NO:24 and a seventh Amplicon consisting of SEQ ID NO:28 and an eighth Amplicon consisting of SEQ ID NO:32 in the sample.

5. The method of claim 4, wherein said assay is a fluorogenic 5' nuclease PCR assay.

6. The method of claim 5, wherein the first Amplicon is detected using a first forward primer consisting of SEQ ID NO:1, a first reverse primer consisting of SEQ ID NO:2, and a first hybridization probe consisting of SEQ ID NO:3 and the second Amplicon is detected using a second forward primer consisting of SEQ ID NO:5, a second reverse primer consisting of SEQ ID NO:6, and a second hybridization probe consisting of SEQ ID NO:7 and the third Amplicon is detected using a third forward primer consisting of SEQ ID NO:9, a third reverse primer consisting of SEQ ID NO:10, and a third hybridization probe consisting of SEQ ID NO:11 and the fourth Amplicon is detected using a fourth forward primer consisting of SEQ ID NO:13, a fourth reverse primer consisting of SEQ ID NO:14, and a fourth hybridization probe consisting of SEQ ID NO:15 and the fifth Amplicon is detected using a fifth forward primer consisting of SEQ ID NO:17, a fifth reverse primer consisting of SEQ ID NO:18, and a fifth hybridization probe consisting of SEQ ID NO:19 and the sixth Amplicon is detected using a sixth forward primer consisting of SEQ ID NO:21, a sixth reverse primer consisting of SEQ ID NO:22, and a sixth hybridization probe consisting of SEQ ID NO:23 and the seventh Amplicon is detected using a seventh forward primer consisting of SEQ ID NO:25, a seventh reverse primer consisting of SEQ ID NO:26, and a seventh hybridization probe consisting of SEQ ID NO:27 and the eighth Amplicon is detected using a eighth forward primer consisting of SEQ ID NO:29, a eighth reverse primer consisting of SEQ ID NO:30, and a eighth hybridization probe consisting of SEQ ID NO:31.

7. The method of claim 1, wherein each Amplicon is detected in a separate reaction tube.

8. The method of claim 4, wherein each Amplicon is detected in a separate reaction tube.

9. The method of claim 1, wherein the sample is from an air monitor.

10. The method of claim 4, wherein the sample is from an air monitor.

* * * * *

SEQUENCE LISTING

<160> NUMBER OF SEQ ID NOS: 32

<210> SEQ ID NO 1
<211> LENGTH: 29
<212> TYPE: DNA
<213> ORGANISM: Francisella tularensis

<400> SEQUENCE: 1
ttgctggata taattttcat tcaaactaa 29

<210> SEQ ID NO 2
<211> LENGTH: 28
<212> TYPE: DNA
<213> ORGANISM: Francisella tularensis

<400> SEQUENCE: 2
aatgtaagca ctgatcattg gataatca 28

<210> SEQ ID NO 3
<211> LENGTH: 30
<212> TYPE: DNA
<213> ORGANISM: Francisella tularensis

<400> SEQUENCE: 3
cgttatccag cgattttctt gttcgttcca 30

<210> SEQ ID NO 4
<211> LENGTH: 110
<212> TYPE: DNA
<213> ORGANISM: Francisella tularensis

<400> SEQUENCE: 4
ttgctggata taattttcat tcaaactaaa actaccgtct acatcaatcg ttatccagcg 60
attttcttgt tcgttccaat actgattatc caatgatcag tgcttacatt 110

<210> SEQ ID NO 5
<211> LENGTH: 27
<212> TYPE: DNA
<213> ORGANISM: Francisella tularensis -continued

```
<400> SEQUENCE: 5

agcttctgca aaaactacaa gaaatct                                          27


<210> SEQ ID NO 6
<211> LENGTH: 28
<212> TYPE: DNA
<213> ORGANISM: Francisella tularensis

<400> SEQUENCE: 6

tcattatgat gctcatagat ttgctcta                                         28


<210> SEQ ID NO 7
<211> LENGTH: 35
<212> TYPE: DNA
<213> ORGANISM: Francisella tularensis

<400> SEQUENCE: 7

agatcaagct acaatagccc aagattacag cgaaa                                 35


<210> SEQ ID NO 8
<211> LENGTH: 105
<212> TYPE: DNA
<213> ORGANISM: Francisella tularensis

<400> SEQUENCE: 8

agcttctgca aaaactacaa gaaatctaca aaaaactata gatcaagcta caatagccca     60

agattacagc gaaactctag agcaaatcta tgagcatcat aatga                     105


<210> SEQ ID NO 9
<211> LENGTH: 28
<212> TYPE: DNA
<213> ORGANISM: Francisella tularensis

<400> SEQUENCE: 9

cagtgaagtt tgaataatct agcgatga                                         28


<210> SEQ ID NO 10
<211> LENGTH: 28
<212> TYPE: DNA
<213> ORGANISM: Francisella tularensis

<400> SEQUENCE: 10

agctatagtt gaaaatgttg agcatcct                                         28


<210> SEQ ID NO 11
<211> LENGTH: 28
<212> TYPE: DNA
<213> ORGANISM: Francisella tularensis

<400> SEQUENCE: 11

cagtgaagtt tgaataatct agcgatga                                         28


<210> SEQ ID NO 12
<211> LENGTH: 92
<212> TYPE: DNA
<213> ORGANISM: Francisella tularensis

<400> SEQUENCE: 12

cagtgaagtt tgaataatct agcgatgata tttgcatttg gaatggacca ttctcatcaa     60

cattaggatg ctcaacattt tcaactatag ct                                    92
```

-continued

<210> SEQ ID NO 13
<211> LENGTH: 29
<212> TYPE: DNA
<213> ORGANISM: Francisella tularensis

<400> SEQUENCE: 13
atagttactc aaaatgcaga tggtgaatc 29

<210> SEQ ID NO 14
<211> LENGTH: 27
<212> TYPE: DNA
<213> ORGANISM: Francisella tularensis

<400> SEQUENCE: 14
gtgatgagaa gagttaaaaa cccatct 27

<210> SEQ ID NO 15
<211> LENGTH: 28
<212> TYPE: DNA
<213> ORGANISM: Francisella tularensis

<400> SEQUENCE: 15
ccaatgcaac tgttgaaaac aatgctgc 28

<210> SEQ ID NO 16
<211> LENGTH: 104
<212> TYPE: DNA
<213> ORGANISM: Francisella tularensis

<400> SEQUENCE: 16
atagttactc aaaatgcaga tggtgaatca gtatggacat accaaaccaa tgcaactgtt 60
gaaaacaatg ctgcaagaga tgggttttta actcttctca tcac 104

<210> SEQ ID NO 17
<211> LENGTH: 28
<212> TYPE: DNA
<213> ORGANISM: Francisella tularensis

<400> SEQUENCE: 17
tatctattat aaccgccaaa gagctcat 28

<210> SEQ ID NO 18
<211> LENGTH: 27
<212> TYPE: DNA
<213> ORGANISM: Francisella tularensis

<400> SEQUENCE: 18
ttcatcacaa ataccaacgt atcttgt 27

<210> SEQ ID NO 19
<211> LENGTH: 34
<212> TYPE: DNA
<213> ORGANISM: Francisella tularensis

<400> SEQUENCE: 19
cgtcacctga tagtgcaact gttactttcg actt 34

<210> SEQ ID NO 20
<211> LENGTH: 108
<212> TYPE: DNA
<213> ORGANISM: Francisella tularensis

<400> SEQUENCE: 20

-continued

```
tatctattat aaccgccaaa gagctcatca ccagcgtcac ctgatagtgc aactgttact     60

ttcgacttag ctattttact cacaagatac gttggtattt gtgatgaa                108


<210> SEQ ID NO 21
<211> LENGTH: 29
<212> TYPE: DNA
<213> ORGANISM: Francisella tularensis

<400> SEQUENCE: 21

taaaagtagc tgtccaaata catggtttt                                      29


<210> SEQ ID NO 22
<211> LENGTH: 28
<212> TYPE: DNA
<213> ORGANISM: Francisella tularensis

<400> SEQUENCE: 22

gctaaaggca aggtttttaa ctatgttt                                       28


<210> SEQ ID NO 23
<211> LENGTH: 33
<212> TYPE: DNA
<213> ORGANISM: Francisella tularensis

<400> SEQUENCE: 23

aaataactgc atacataagc gcaccaatca agc                                 33


<210> SEQ ID NO 24
<211> LENGTH: 99
<212> TYPE: DNA
<213> ORGANISM: Francisella tularensis

<400> SEQUENCE: 24

taaaagtagc tgtccaaata catggttttg gtaggaaata actgcataca taagcgcacc     60

aatcaagcct aaaacatagt taaaaacctt gcctttagc                           99


<210> SEQ ID NO 25
<211> LENGTH: 29
<212> TYPE: DNA
<213> ORGANISM: Francisella Tularensis

<400> SEQUENCE: 25

ctcatcaacc ttatgagctc ttacataag                                      29


<210> SEQ ID NO 26
<211> LENGTH: 26
<212> TYPE: DNA
<213> ORGANISM: Francisella tularensis

<400> SEQUENCE: 26

taagagacaa tctgcagaga ttttgc                                         26


<210> SEQ ID NO 27
<211> LENGTH: 29
<212> TYPE: DNA
<213> ORGANISM: Francisella tularensis

<400> SEQUENCE: 27

caactatttc ggtcgcctta gccttagcc                                      29


<210> SEQ ID NO 28
<211> LENGTH: 94
```

-continued

```
<212> TYPE: DNA
<213> ORGANISM: Francisella tularensis

<400> SEQUENCE: 28

ctcatcaacc ttatgagctc ttacataagc attttcaact atttcggtcg ccttagcctt     60

agcctcacgc aaaatctctg cagattgtct ctta                                 94


<210> SEQ ID NO 29
<211> LENGTH: 29
<212> TYPE: DNA
<213> ORGANISM: Francisella tularensis

<400> SEQUENCE: 29

ctacttcttc agccttaaca gctttaaac                                       29


<210> SEQ ID NO 30
<211> LENGTH: 28
<212> TYPE: DNA
<213> ORGANISM: Francisella tularensis

<400> SEQUENCE: 30

aacaagtttc gcattaatgt tgtaagtc                                        28


<210> SEQ ID NO 31
<211> LENGTH: 33
<212> TYPE: DNA
<213> ORGANISM: Francisella tularensis

<400> SEQUENCE: 31

tggcgcatat ttatcaagag cttcttcaac aac                                  33


<210> SEQ ID NO 32
<211> LENGTH: 106
<212> TYPE: DNA
<213> ORGANISM: Francisella tularensis

<400> SEQUENCE: 32

ctacttcttc agccttaaca gctttaaacc caataaaaaa tggcgcatat ttatcaagag     60

cttcttcaac aacagttgga cttacaacat taatgcgaaa cttgtt                   106
```